United States Patent [19]
Blackburn

[11] Patent Number: 6,010,489
[45] Date of Patent: Jan. 4, 2000

[54] INCONTINENCE APPLIANCES FOR MALES

[75] Inventor: Roger Blackburn, Oxford, United Kingdom

[73] Assignee: D.B.T. Medical Limited, Oxon, United Kingdom

[21] Appl. No.: 09/052,931

[22] Filed: Apr. 1, 1998

[30] Foreign Application Priority Data

Apr. 1, 1997 [GB] United Kingdom .................... 9706507

[51] Int. Cl.[7] ...................................................... A61F 5/44
[52] U.S. Cl. ............................ 604/353; 604/351; 604/349
[58] Field of Search ..................... 128/DIG. 26, DIG. 15; 604/349–353

[56] References Cited

U.S. PATENT DOCUMENTS 2,484,356  10/1949  Ribeiro et al. ........................... 604/353
4,200,102   4/1980  Duhamel et al. ........................ 604/353

FOREIGN PATENT DOCUMENTS 2185402  7/1987  United Kingdom ................... 604/353

*Primary Examiner*—Mark O. Polutta
*Attorney, Agent, or Firm*—Diller, Ramik, Wight, PC

[57] ABSTRACT

A male incontinence device has rails formed on its waistband, through which the ends of the leg straps can be looped and secured in a desired position by clips. At their front ends the straps are attached to a ring which forms part of the bib of the waistband. A grommet push fitted into the ring from the inside has inner and outer flanges at its ends. The outer flange serves for attachment of a urine collection cone, whereas the inner flange provides for attachment of a seal member. The seal member has a U-section periphery for engaging it over the inner flange of the grommet, and provides a thin, apertured membrane capable of forming a comfortable seal with the penis of the user.

10 Claims, 4 Drawing Sheets

INCONTINENCE APPLIANCES FOR MALES

BACKGROUND OF THE INVENTION

Males suffer from varying degrees of incontinence and many different designs of appliance have been designed to meet those needs. One particular problem that an important percentage of users suffer from is known as the receding penis syndrome (retracted penis). In the 1950's a urinal was designed known as a pubic pressure urinal which created pressure around the pubic area which has the advantage of forcing the penis forward and making it easier to conduct urine away from the body without the patient becoming wet. Such urinals are still widely used but current designs have certain disadvantages. One of the major disadvantages is the variety of sizes and components needed to fit each individual patient satisfactorily, and there is a need for an incontinence appliance which can be easily fitted and adjusted ideally by the patient himself.

SUMMARY OF THE INVENTION

The present invention seeks to provide a male incontinence device particularly, but not necessarily, a pubic pressure urinal which can be easily adjusted to suit the individual wearer. In accordance, therefore, with one aspect thereof the invention seeks to provide a male incontinence device having a waistband and at least two straps with free ends requiring attachment to the waistband at longitudinally spaced positions thereof, characterised in that the waistband includes a rail for each strap, and each strap free end is terminated by a clip in relation to which the strap is longitudinally adjustable, the clips being initially adjustable longitudinally of their respective rails and operable in their adjusted positions to render them laterally immovable.

The waistband may be of elastic material, the rails being likewise elastic. Alternatively the waistband may be substantially inelastic in which case it is preferred for the rails to be substantially inelastic also.

The rails may be formed in common from a single piece of material attached to the waistband but more usually they will be formed of respective pieces of material spaced longitudinally around the waistband. They may be an integral part of the waistband but it is preferred that they are formed by elongate material sewn or otherwise attached around the outside of the waistband.

Each rail may comprise several loops arranged end-to-end and any one of which may serve for the adjustable attachment of a said clip.

Other aspects and preferred features of the invention will become apparent from the following description of a male incontinence appliance in accordance with the invention which is given, by way of example only, with reference to the accompanying drawings.

BRIEF DESCRIPTION OF THE DRAWINGS

FIG. 3b is a side elevational view of the clip of FIG. 3a;

DESCRIPTION OF THE PREFERRED EMBODIMENTS

Figure 1:
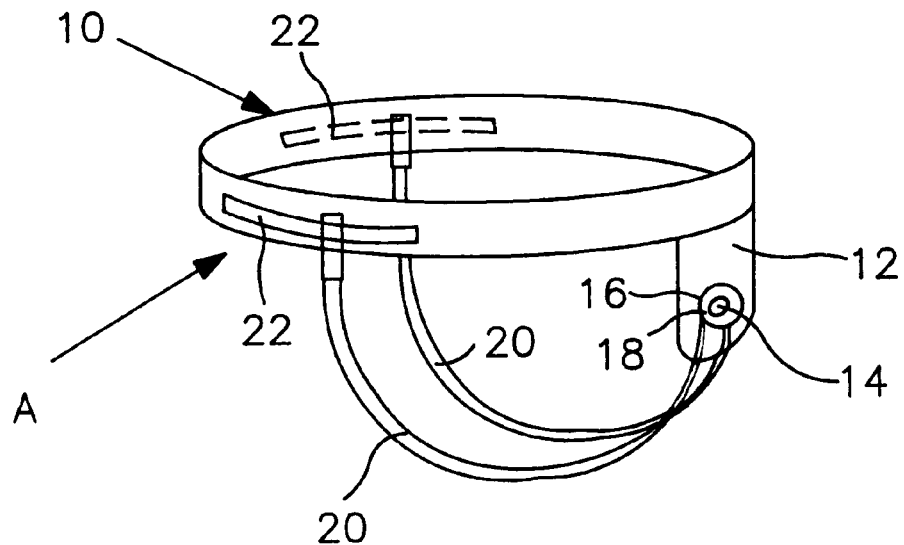
FIG. 1 is a general view of the appliance showing two straps having free ends adjustably attached to the waistband of the appliance.

Referring firstly to FIG. 1 of the drawings, a pubic pressure urinal has a waistband 10 of elasticated webbing material to the front of which a pendant bib 12 is attached. In known manner the bib is formed with a hole 14, and a grommet 16 of natural gum stock rubber or similar material is push-fitted into the hole so as to provide an annular flange on each side of the bib. The flange on the outer side of the bib is shown and indicated by the reference number 18.

For use of the appliance a seal member having a hole through which the penis of the wearer may extend is attached to the inner flange of the grommet, and a cone to which a urine collection bag may be attached is fitted to the outer flange 18 in surrounding relation to the cone and the wearer's penis. These components each make a fluid tight engagement with the grommet; they are shown in detail in relation to FIGS. 5 and 6.

In order to apply backward pressure to the bib 12 and thereby to the pubic area two elasticated straps 20 are attached to the big adjacent its hole 14 and from there extend backwardly and outwardly to separate attachment with the waistband 10 at their other ends.

Figure 2:
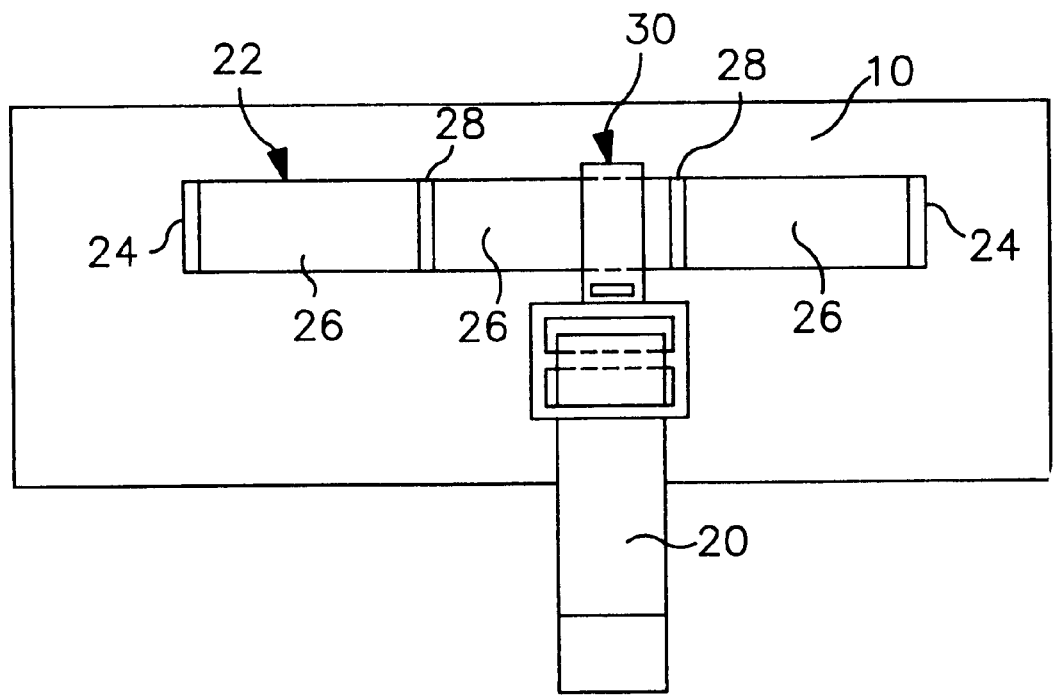
FIG. 2 is an enlarged view of the portion of the waistband indicated by the arrow A in FIG. 1.
Figure 3A:
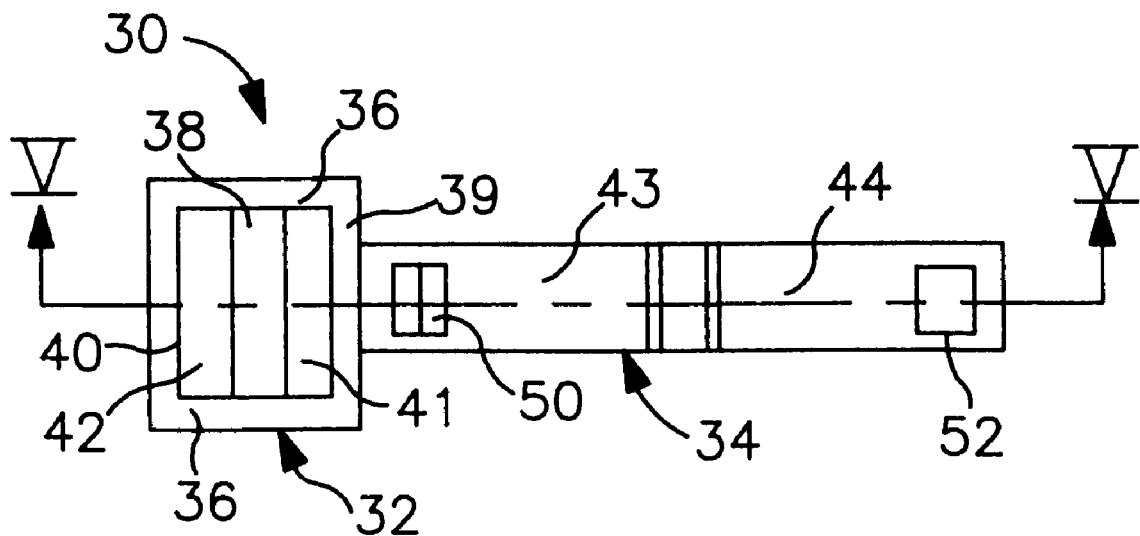
FIG. 3a is a plan view of a clip used for making the attachment, as it is manufactured and before fitting.
Figure 3B:
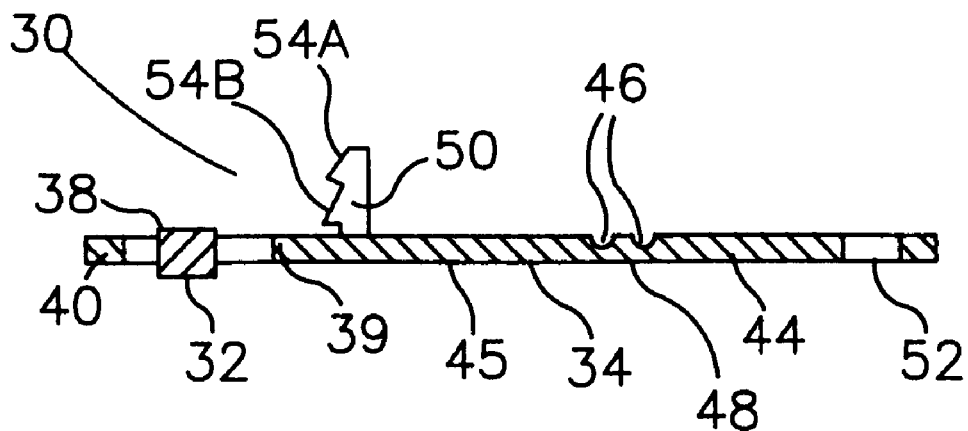
Figure 4:
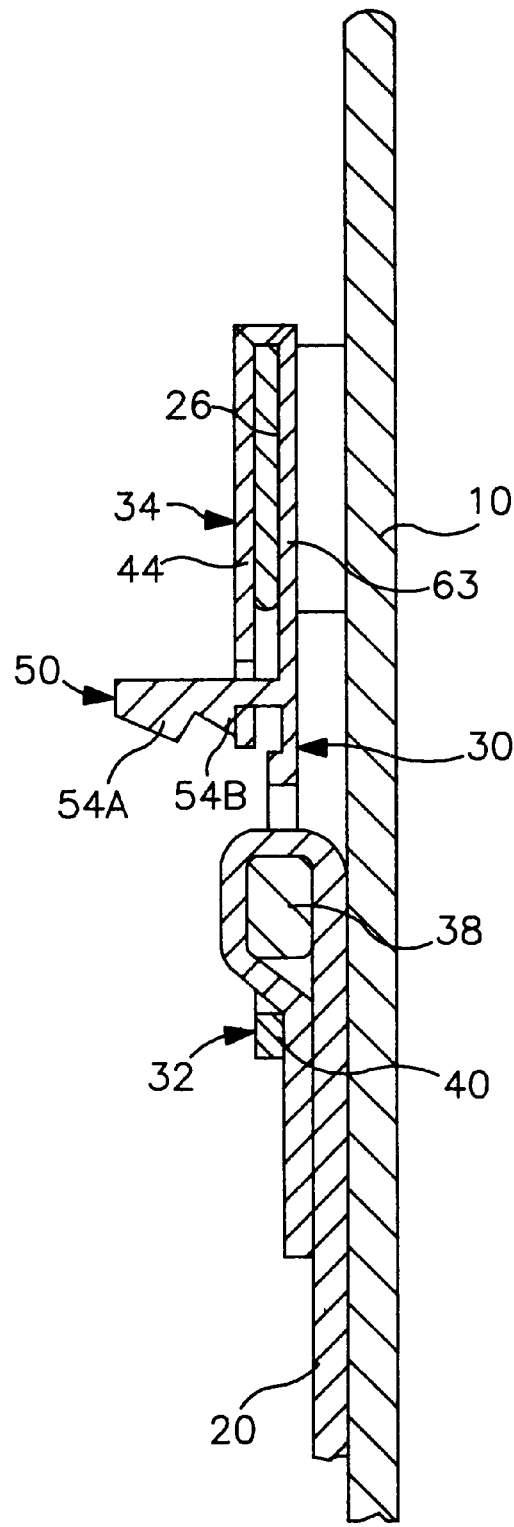
FIG. 4 shows the clip in relation to a strap and to a rail of the waistband after fitting.

The free back ends of the straps 20 are adjustably attached to the waistband 10 by the user of the appliance the detail of the attachment being apparent from FIGS. 2 to 4 in relation to which this description is now given. For each strap a rail 22 is formed on the waistband by a length of elasticated webbing which is sewn to the outside of the waistband as shown. The rail is formed between vertical lines of stitching 24 at its ends, and provides a series of free loops 26 arranged end-to-end and separated by further lines of stitching 28. In the embodiment shown each rail has three loops formed between four lines of stitching 24, 28. Typically the loops are each 4 cms in length.

The rails provide for laterally adjustable attachment of the free ends of respective straps 20 as will be described. The attachments are made by a pair of clips 30 of which one is shown as moulded in plan view in FIG. 3A and on a central longitudinal section in FIG. 3B.

Referring now to FIGS. 3A, 3B, each clip 30 is moulded in the generally planar configuration shown, from a suitable thermoplastics material such as polypropylene. It has a relatively wide and rectangular buckle portion 32, and a narrower, elongate and rectangular clip portion 34 attached along one side of the buckle portion.

The buckle portion 32 has three spaced and parallel bars extending between cross bars 36 at their ends. In FIGS. 3A, 3B the central one of the parallel bars is denoted 38, the inner and outer parallel bars being denoted 39 and 40 respectively. The parallel and cross bars together define two parallel rectangular slots 41, 42 through which a single thickness of a belt 20 may be passed.

The clip portion 34 of each strap 20 has inner and outer rectangular parts 43, 44 joined by living hinges 46 on either side of a short rectangular segment 48. A post 50 stands up from the inner part 43, and is insertable through a hole 52 formed through the outer part 44 when the latter is folded over the inner part by articulation at the living hinges 46.

On its surface remote from the outer clip part 44, that is to say, the surface facing the buckle portion 32, the post 50 is formed with a pair of upper and lower barbs 54A, 54B. The outer part 44 of the clip can be snap engaged in succession past both barbs, but because of the greater severity of the lower barb 54B in relation to the upper barb 54A, the outer part can be released more easily from the upper barb than from the lower barb.

In use of the appliance the user fits the waistband 10 and the bib 12 in normal manner after fitting the ends of the belts 20 to the buckle portions 32 of the clips in the well known configuration shown in FIG. 4. The user then passes each strap in turn under tension between his legs, and inserts the clip portion 34 of the clip upwardly through that loop 26 of the respective rail 22 which appears to offer him the greatest degree of comfort. He then folds the outer part 44 of the clip portion over the rail, and snaps it behind the first barb 54A on the post.

At that time the clip is capable of withstanding the tension in the strap but is attached to the rail sufficiently loosely to allow the user to adjust it laterally (within the length of the loop) for maximum comfort; (at this time) the strap may also be adjusted longitudinally in the buckle portion as desired. If the loop 26 which he has chosen proves to be unsatisfactory the user can open the clip, reposition it in a more suitable loop, and reclose and adjust it as required.

When he is satisfied with the lateral portion of each clip in relation to the waistband, the user presses inwardly on the outer part 44 of each clip so that it snap-engages behind the lower barb 54B on the post 50. In this position the clip tightly clamps the strap 20 between its inner and outer parts 43, 44 as is shown in FIG. 4, so preventing the possibility of any further relative lateral movement. Moreover, the clip is locked closed and cannot open inadvertently thereafter.

In this way a secure attachment is formed between each strap and the waistband at an optimised position. It should be noted that longitudinal adjustment of each strap in its clip 30 is still possible, but in a possible modification of the embodiment shown the outer part 44 of each clip is arranged to engage the strap material at the buckle portion 32 so as additionally to lock the strap against longitudinal movement.

Further security against longitudinal movement of the belt may additionally or alternatively be provided by enlarging the central bar 38 of each clip as is shown in FIG. 4 and/or by forming a series of serrations or protrusions (not shown) along the underside of the outer bar 40.

Figure 5:
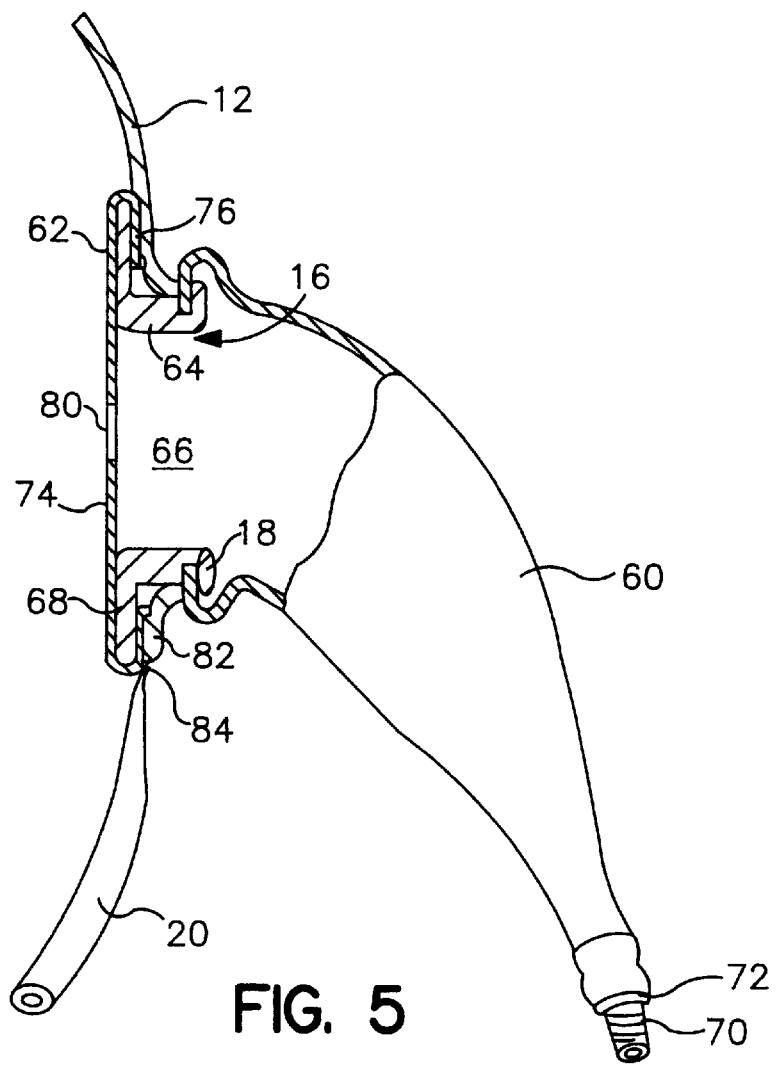
FIG. 5 shows the arrangement of the device in the pubic area.

FIG. 5 shows a preferred arrangement of the grommet 16 and its attachment to the bib 12 and straps 20. Also shown is the cone 60 and a seal member 62 which appears in further detail in FIG. 6.

The grommet 16 has a generally cylindrical central core 164 formed with a through hole 66 which is large enough to accept the wearer's penis with clearance. Radially extending flanges are integrally formed at each of the cone, the flange 18 at the outer end of the grommet (in relation to the user) being the smaller in diameter. The cone is thickened over part of its length adjacent to the inner flange 68 so that a narrow groove 70 is formed around the cone adjacent to the outer flange 18 into which the free edge of a cone 60 may be engaged as shown. At its free distal end the cone carries a screw-threaded connection piece 70 with associated 'O' ring 72 by means of which a urine connection bag may be attached. The conduit and bag may be conventional and are therefore not described.

Figure 6:
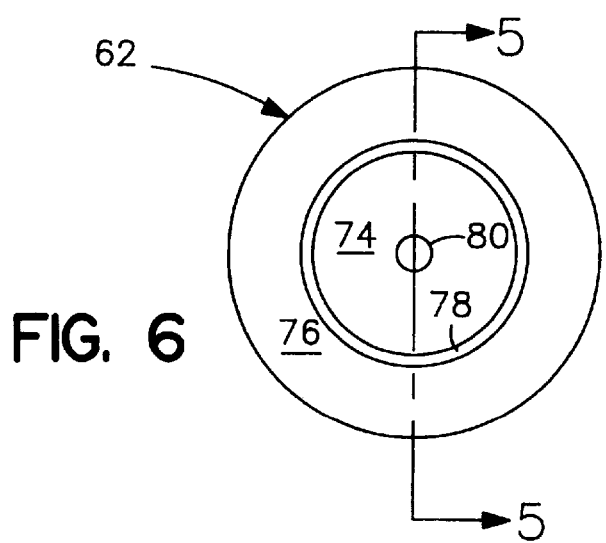
FIG. 6 shows a seal member which is included in the arrangement of FIG. 5.

As can be seen in detail from FIG. 6 which shows it as seen looking from outside, the seal member 62 is circular and formed of a plane membrane 74 from the periphery of which a narrow annulus 76 of material extends radially inwards to its own free edge 78. The disc and annulus are in parallel relation and accordingly form a U-section peripheral margin (not referenced) The free edge 78 is rolled to form a rim which assists handling.

The annulus 76 is of relatively thick material for example 0.03", whereas the material of the membrane 74 is much thinner, a preferred thickness being within the range 0.005–0.010, especially 0.007". The front disc, however, is formed with a central hole 80 of typically 0.35" diameter.

The seal member 62 is sized to fit over the inner flange 68 of the grommet 16 in the manner shown in FIG. 5. This can easily be achieved by the wearer by simple manipulation. The narrow annulus 76 of the seal member then lies against the inner face of the flange 68, the flange 68 itself being a tight but distortion-free fit within the U-section margin of the seal diaphragm. Also shown in FIG. 5 is the bib 12 and its retaining ring 82 by which the grommet 16 and, by means of it, the cone 60 (and attachments) and the seal member 62 are supported in relation to the penis of the user.

The retaining ring 82 of the bib 12 has the ends of the straps 20 made off to it at the required spacing preferably by being sewn in to slits 84 made in the outer edge of the ring.

The device can be simply fitted for use by fitting the seal member 62 on to the inner flange 68 of the grommet 16, and then pushing the grommet 16 into position in the retaining ring 82 of the bib 12, as shown in FIG. 5. The device is then ready for fitting to the user, who inserts his penis through the hole 80 of the seal diaphragm and adjust and tightens the straps 20 to achieve maximum comfort and the required amount of backward pressure around the pubic area. The cone 60 and its attachments can then be added at a convenient time.

The seal member 62 is made from latex rubber by calendering and bonding techniques. By virtue of its substantial thinness however the membrane 74 is able to undergo a considerable degree of lateral deformation by which it is able to conform itself to the position and size of the users penis whilst maintaining a liquid-tight seal at all times. A secure but comfortable fit is therefore assured, with no apparent constriction caused by the engagement. Moreover, the seal member can be easily detached when required for cleaning or replacement. This is in contrast with known diaphragm seals which are bonded in position and therefore are difficult to replace.

Whilst the embodiment of the invention particularly described provides lateral and longitudinal adjustment of its leg straps 20 by means of rails 22 on the waistband 10 and clips 30 associated individually with the straps, other arrangements may alternatively be used within the scope of the invention. For example, the straps may be terminated by lengths of webbing to which lengths of VELCRO (Registered Trade Mark) are stitched. The same material may also be attached to the waistband itself, to provide the required longitudinal and/or lateral adjustment.

Although a preferred embodiment of the invention has been specifically illustrated and described herein, it is to be understood that minor variations may be made in the apparatus without departing from the spirit and scope of the invention, as defined the appended claims.

I claim:

1. A male incontinence device comprising a waistband and at least two straps with free ends, means for adjustably attaching the free ends of the two straps to the waistband at longitudinally spaced positions thereof, the waistband adjustable attaching means includes a rail for each strap carried by said waistband, each strap free end includes a clip in relation to which an associated strap is longitudinally adjustable, the clips being initially adjustable longitudinally of their respective rails, and means operable in the adjusted positions of the clips to render the clips laterally immovable along the rails.

2. The device in accordance with claim 1 wherein the waistband and the rails are made of elastic material.

3. The device in accordance with claim 1 wherein the waistband and the rails are made of substantially inelastic material.

4. The device in accordance with claim 1 wherein the rails are formed of separate pieces of material spaced longitudinally apart around the waistband.

5. The device in accordance with claim 1, wherein the rails are an integral part of the waistband.

6. The device in accordance with claim 1 wherein each rail includes several loops arranged end-to-end and any one of which may serve for the adjustable attachment of a said clip.

7. The device in accordance with claim 1 wherein each clip includes a buckle portion in relation to which at least one of the at least two straps is longitudinally adjustable, and a clip portion operable between a first position at which the clip may be adjusted longitudinally in relation to its respective rail and a second position at which it holds the clip laterally immovable on the rail.

8. The device in accordance with claim 7 wherein the clip portion in its second position engages the strap to lock it against longitudinal movement in relation to the buckle portion.

9. The male incontinence device as defined in claim 1 wherein said waistband includes a front part having a depending bib formed with an aperture, said adjustable attaching means are located at opposite sides of said aperture, a grommet having a core with an opening therethrough, said grommet having inner and outer flanges and seated between the flanges is a peripheral wall portion defining the aperture of the bib, the outer flange serving for separable attachment of a urine collection cone, a seal member having a substantially thin membrane surrounded by a generally U-shaped periphery, the seal member being separately attached to the inner flange of the grommet at said U-shaped periphery, said membrane being disposed in substantially uni-planar relationship across the opening of the grommet, and the membrane having an opening and being conformable to the position and size of the wearer's penis extending through the opening of the membrane and into the opening of the grommet.

10. A male incontinence device comprising a waistband having at a front part thereof a depending bib formed with an aperture, leg straps attached to the bib adjacent the aperture, means for adjustable attaching the leg straps to the waistband, a grommet having a core with an opening therethrough, the grommet having inner and outer flanges and seated between the flanges is a peripheral wall portion defining the aperture of the bib, the outer flange serving for separable attachment of a urine collection cone, a seal member having a substantially thin membrane surrounded by a generally U-shaped periphery, the seal member being separably attached to the inner flange of the grommet at said U-shaped periphery, said membrane being disposed in substantially uni-planar relationship across the opening of the grommet, and the membrane having an opening and being conformable to the position and size of the wearer's penis extending through the opening of the membrane and into the opening of the grommet.

* * * * *